(12) United States Patent
Jeannin

(10) Patent No.: US 9,926,046 B2
(45) Date of Patent: Mar. 27, 2018

(54) DEVICE FOR MOORING A WATER CRAFT TO A MOORING BERTH OF A PONTOON, AND CORRESPONDING PONTOON

(71) Applicant: SAVOYE, Dijon (FR)

(72) Inventor: Remy Jeannin, Fixin (FR)

(73) Assignee: SAVOYE, Dijon (FR)

(*) Notice: Subject to any disclaimer, the term of this patent is extended or adjusted under 35 U.S.C. 154(b) by 0 days.

(21) Appl. No.: 15/259,873

(22) Filed: Sep. 8, 2016

(65) Prior Publication Data
US 2017/0066505 A1 Mar. 9, 2017

(30) Foreign Application Priority Data
Sep. 8, 2015 (FR) ..................................... 1558330

(51) Int. Cl.
| B63B 21/00 | (2006.01) |
| A61K 38/12 | (2006.01) |
| A61K 8/64 | (2006.01) |
| C07K 14/705 | (2006.01) |
| C07K 7/64 | (2006.01) |
| C07K 5/087 | (2006.01) |

(52) U.S. Cl.
CPC ................ B63B 21/00 (2013.01); A61K 8/64 (2013.01); A61K 38/12 (2013.01); C07K 5/0812 (2013.01); C07K 7/64 (2013.01); C07K 14/705 (2013.01); B63B 2021/004 (2013.01)

(58) Field of Classification Search
CPC .............................. B63B 21/045; B63B 21/00
USPC ................................................... 114/230.14
See application file for complete search history.

(56) References Cited

U.S. PATENT DOCUMENTS

| 5,711,242 A | 1/1998 | Blanc et al. |
| 7,131,387 B1 * | 11/2006 | Czipri ................... B63B 21/045 |
| | | 114/218 |

(Continued)

FOREIGN PATENT DOCUMENTS

| DE | 932294 C | 1/1956 |
| EP | 2316721 A1 | 5/2011 |

(Continued)

OTHER PUBLICATIONS

French Preliminary Search Report and Written Opinion dated Jun. 30, 2016 for French Application No. 1558330, filed Sep. 8, 2015.

(Continued)

*Primary Examiner* — Stephen P Avila
(74) *Attorney, Agent, or Firm* — David D. Brush; Westman, Champlin & Koehler, P.A.

(57) ABSTRACT

A mooring device for mooring a water craft to a mooring berth. The mooring device includes an engaging element borne by the water craft or the mooring berth, and a lock borne by the mooring berth or the water craft, respectively. The lock includes two catch bars spaced out and extending vertically, at least a part of the engaging element being adapted to engaging between the two bars so as to be held by the lock and enabling the mooring of the water craft to the mooring berth. The catch bars are mobile relative to each other between a locking position in which the catch bars are brought closer to each other and maintain the engaging element and an unlocking position in which the catch bars are moved apart to enable the removal or insertion of the engaging element.

21 Claims, 10 Drawing Sheets

(56) References Cited

U.S. PATENT DOCUMENTS

| | | | |
|---|---|---|---|
| 7,827,924 B1 * | 11/2010 | Perez | ................... B63B 21/00 114/230.15 |
| 7,992,508 B1 | 8/2011 | Norton | |
| 2012/0285359 A1 * | 11/2012 | Cichoski | ................ B63B 21/00 114/230.15 |

FOREIGN PATENT DOCUMENTS

| | | | |
|---|---|---|---|
| EP | 2520485 | A1 | 11/2012 |
| EP | 2818396 | A1 | 12/2014 |
| WO | 2009073897 | A2 | 6/2009 |

OTHER PUBLICATIONS

French Preliminary Search Report and Written Opinion dated Jun. 30, 2016 for French Application No. 1558899, filed Sep. 8, 2015.
European Search Report dated Jan. 20, 2017 for corresponding European Application No. 16185782.

* cited by examiner

DEVICE FOR MOORING A WATER CRAFT TO A MOORING BERTH OF A PONTOON, AND CORRESPONDING PONTOON

1. CROSS-REFERENCE TO RELATED APPLICATIONS

This Application claims priority to and the benefit of French Patent Application 1558330, filed Sep. 8, 2015, the content of which is incorporated herein by reference in its entirety.

2. FIELD OF THE DISCLOSURE

The disclosure relates to a device for mooring a water craft to a mooring berth of a pontoon or a wharf, for example.

The disclosure also relates to a pontoon equipped with one or more mooring devices.

The present disclosure can especially be implemented at sea, on lakes or rivers and is especially but not exclusively adapted to pleasure boats or recreational boats.

3. TECHNOLOGICAL BACKGROUND

The mooring of a water craft, for example a pleasure boat or a sailboat, is the final phase of a berthing maneuver. It consists in maintaining the water craft against a pontoon, for example, and attaching it to the pontoon in order to limit the motions of the water craft relative to the pontoon.

A known technique, illustrated in FIG. 1, consists in tying the water craft (not shown) to a pontoon C by using a rope B and one or more mooring points A which can take the form of a cleat, a bollard or a ring. The number of mooring points depends on the size of the water craft.

One drawback of this approach is that it requires the presence of one or more persons. In addition, since the water craft is subjected to the movements of the water (swells), such a mooring maneuver has risks for the individuals present. Besides, such mooring can be insecure if there is a relatively high risk of theft of the water craft.

To overcome some of these drawbacks, the patent application WO2009/073897 proposes the use of a locking mechanism which corresponds to a vertical bar fixedly attached to a pontoon, and placed between the guiding elements of the bow of a boat having a general V-shape. A hook situated on the bow of the boat is used to grip the vertical bar so as to irreversibly moor the water craft to the pontoon.

Besides, the pontoon has a hinge which enables a locking mechanism to follow the movements of the water (due to the tide and/or the water swell).

This approach uses numerous mechanical parts which make manufacture complicated and costly, and greatly increases the risks of dysfunction.

There is therefore a major need for improving water craft mooring devices to optimize security, manufacturing costs and maintenance in a simple and effective way.

4. SUMMARY

An exemplary aspect of the present disclosure relates to a mooring device for mooring a water craft to a mooring berth comprising:
  an engaging element borne by the water craft or the mooring berth and
  a lock borne by the mooring berth or the water craft respectively,
  said lock comprising two catch bars spaced out and extending vertically, at least a part of the engaging element being adapted to getting engaged between the two bars so as to be held by said lock and enabling the mooring of the water craft to the mooring berth.

According to an exemplary embodiment, said catch bars are mobile relative to one another between a locking position (closed) in which the catch bars are brought closer to each other and maintain said engaging element and an unlocking position (open) in which the catch bars are moved apart to enable the removal (or release) or insertion of said engaging element.

Thus, the implementing of mobile catch bars facilitates the mooring and the release of a water craft to and from a mooring berth situated on a pontoon for example.

The catch bars are connected to one another by means of at least one pivot link enabling a movement of jaws relative to each other.

The engaging element, for example borne by a water craft, can be placed between the open catch bars and then, once these catch bars are closed, they can be maintained by the catch bars, enabling easy and reliable mooring of the water craft to the pontoon. The opening of the catch bars permits the withdrawal of the engaging element and the moving away of the water craft to a distance from the pontoon.

The catch bars which are, for example, fixedly attached to the pontoon, extend in a plane perpendicular to the surface of the pontoon and are, for example, linked to one another on at least one of their extremities. Preferably, they are linked to one another at each of their extremities so as to provide for reliable mooring of the water craft.

In one alternative, the catch bars are fixed to the water craft while the engaging element is fixedly attached to the pontoon.

The use of such catch bars offers a degree of freedom to the engaging element disposed and held between the catch bars and reduces the forces applied to the mooring device in the event of rough waters, for example. Because of their shape, the catch bars indeed enable the engaging element to move vertically between these catch bars so as to follow the movements of the water (due to tides and/or water swells).

The space between the catch bars also provides for lateral play of the engaging element.

Besides, these catch bars are adapted to receiving a variety of heights of engaging element, these heights depending on the type of boat.

Such a mooring device has simple structure and functioning and facilitates the berthing and maneuvers for mooring a water craft to a pontoon (and inversely for unmooring the water craft).

The mooring of the water craft is furthermore secured.

Besides, such a mooring device can be easily adapted to an existing pontoon or to any type of water craft.

According to one particular aspect of the disclosure, said engaging element comprises a first end portion connected by a central portion of small width/section to a second end portion, this second portion being connected to the water craft or to the mooring berth.

Thus, the engaging element comprises a first end portion that is wider than the central portion. For example, it can be a T-shaped element, the horizontal bar of the T being the first end portion and the vertical bar of the T being the central portion of reduced width.

Other shapes can be implemented, for example a Y shape.

According to one particular aspect of the disclosure, said second end portion has an opening for cooperating with a berthing pole or a pole for moving the water craft to a distance.

Thus, the second end portion of the engaging element, connected to the water craft for example, has an opening for cooperating with a pole being used by the pleasure-boat user situated on the pontoon so as to place the engaging element between the catch bars during the mooring or push or move away the engaging element from the catch bars when the water craft starts moving. Such a pole can be automatic.

According to one particular aspect of the disclosure, in their locking position, the catch bars are situated on either side of said central portion.

Thus, in this position, the catch bars close in on the central portion of the engaging element, thus securing the mooring of the water craft.

According to one particular aspect of the disclosure, said first end portion is disposed on a first side of the catch bars, the space between the catch bars in the locking position being smaller than the width of said first end portion.

According to one particular aspect of the disclosure, the space between the catch bars in the locking position is greater than the width of said central portion.

According to one particular aspect of the disclosure, the space between the catch bars in the locking position is smaller than the width of said second end portion.

Thus, in the locking position of the catch bars, the space between them is smaller than the width of the first and second end portions of the engaging element. As a consequence, the catch bars are blocked between the first and second end portion of the engaging element. A configuration of this kind makes it possibly to solidly tie the water craft to the mooring berth and to get rid of or at the very least limit the movements of the water craft along an axis perpendicular to the axis of the catch bars.

Besides, in this locking position, the space between the catch bars is greater than the width of the central portion and therefore enables a vertical shift, i.e. a shift along an axis parallel to the axis of the catch bars, of the engaging element between the catch bars. This configuration therefore enables the water craft to move vertically according to the movement of the water (swells, tide) and thus limit the mechanical strains/forces applied to the device.

According to one particular aspect of the disclosure, the engaging element comprises a first fixed part fixedly attached to the water craft or the mooring berth and a second part mounted detachably on the first fixed part and intended to cooperate with the lock.

The use of such a detachable part enables the insertion, by hand, of the first end portion of the engaging element between the catch bars of the lock without having to shift the bars between the open (unlocking) position and the closed (locking) position. Such engaging element is compatible with a device that has mobile catch bars (in this case it is not necessary to detach the detachable part) but also with the device for which the catch bars are fixed.

According to another particular aspect of the disclosure, the engaging element comprises a first fixed part fixedly attached to the water craft or to the mooring berth and a second part mounted pivotingly on the first fixed part and designed to cooperate with the lock.

The use of such a pivoting part enables the insertion of the first end portion of the engaging element between the bars of the lock without having to shift the bars between the open/unlocking position and the closed/locking position. It is necessary only to make this pivoting part pivot by 90° (vertical position) in order to make the first extremity part of the engaging element pass beyond the catch bars and then pivot the pivoting part again by 90° (horizontal position) to block the engaging element between the catch bars and thus enable the secured mooring of the water craft.

Such engaging element is equally compatible with a device having mobile catch bars or fixed catch bars.

According to one particular aspect of the disclosure, each catch bar has, on at least one of its ends, a bracket mounted pivotingly with a corresponding bracket of the other catch bar, the catch bars and the brackets thus forming two mobile jaws.

The use of brackets at one extremity or at each of the extremities of the catch bars forms two jaws which are used to ensure secured mooring of a water craft to a mooring berth in a simple and inexpensive way.

According to one particular aspect of the disclosure, said lock comprises an actuator acting on at least one bracket of each jaw.

According to one particular aspect of the disclosure, said actuator comprises a pair of tie-rods mounted pivotingly about a same axis at a first of their extremities, each of said tie-rods being mounted pivotingly at a second extremity on a distinct bracket of one of said jaws.

According to one particular aspect of the disclosure, said tie-rods are mounted pivotingly at their first extremity on a support mobile in translation so as to make the angle of aperture between the two tie-rods vary.

According to one particular aspect of the disclosure, the support is connected to an actuating cam by a rod.

According to one particular aspect of the disclosure, said cam is moved by a motor.

Thus, the opening and closing of the jaws are automatic and facilitate the mooring maneuver.

In one variant of the disclosure, said cam is shifted by a handle connected to said cam by a shaft.

Thus, the opening and closing of the jaws can be done by hand.

According to one particular aspect of the disclosure, the device also comprises a guide for centering and guiding the engaging element towards the lock situated on either side of the catch bars.

Thus, such guide simplifies the engagement of the engaging element in the lock so as to facilitate the mooring maneuver. The guide is useful for a pleasure-boat owner or boater who might be alone on board his water craft or during difficult weather conditions especially.

According to one particular aspect of the disclosure, said lock is mobile relative to said mooring berth when they are borne by this mooring berth.

According to one particular aspect of the disclosure, said lock is borne by at least one carriage capable of shifting in translation on a rail, said rail being mounted so as to be fixed to the mooring berth.

Thus, the mooring device comprises a shifting element for shifting the lock on the mooring berth, a pontoon for example. Such shifting element provides the device with increased flexibility.

The mooring device of the disclosure can be adapted to any type of installation for receiving ships at sea, on a river, or a lake especially.

The disclosure also relates to a pontoon comprising one or more mooring devices as described above.

5. LIST OF FIGURES

Other features and advantages shall appear from the following description given by way of an indicative and non-exhaustive example and from the appended drawings of which:

6. DETAILED DESCRIPTION OF EMBODIMENTS OF THE INVENTION

The mooring device of the disclosure comprises, in the embodiment described below, a lock in the form of two catch bars spaced out and fixedly attached to a harbor installation (a pontoon for example) and an engaging element which is fixedly attached to a water craft (a pleasure boat for example) to be moored to the harbor installation and intended to get engagement between the catch bars.

By their shape, the bars indeed enable the engaging element to move vertically between the bars so as to follow the movements of the water (due to the tides and/or swells).

The first and second embodiments described below have an identical principle of operation in which the lock borne by the pontoon comprise two jaws that are mobile relative to each other in order to grip the engaging element borne by a water craft.

The third and fourth embodiments describe a principle of operation different from that of the first two embodiments since the two jaws are fixed and it is the engaging element borne by a water craft that must be shifted and/or handled in order to cooperate with the jaws of the pontoon.

6.1 Description of a First Embodiment

Figure 1:
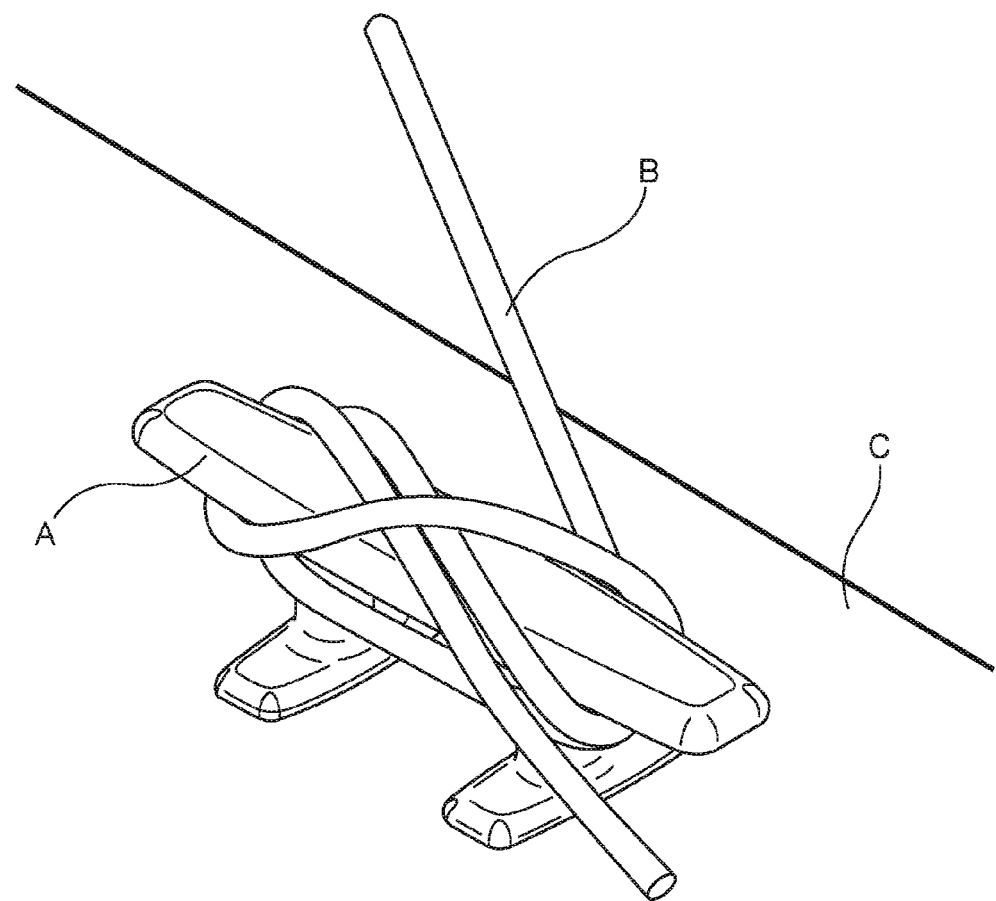
FIG. 1 is a three-quarter view of a mooring device as described in the prior art.
Figure 2:
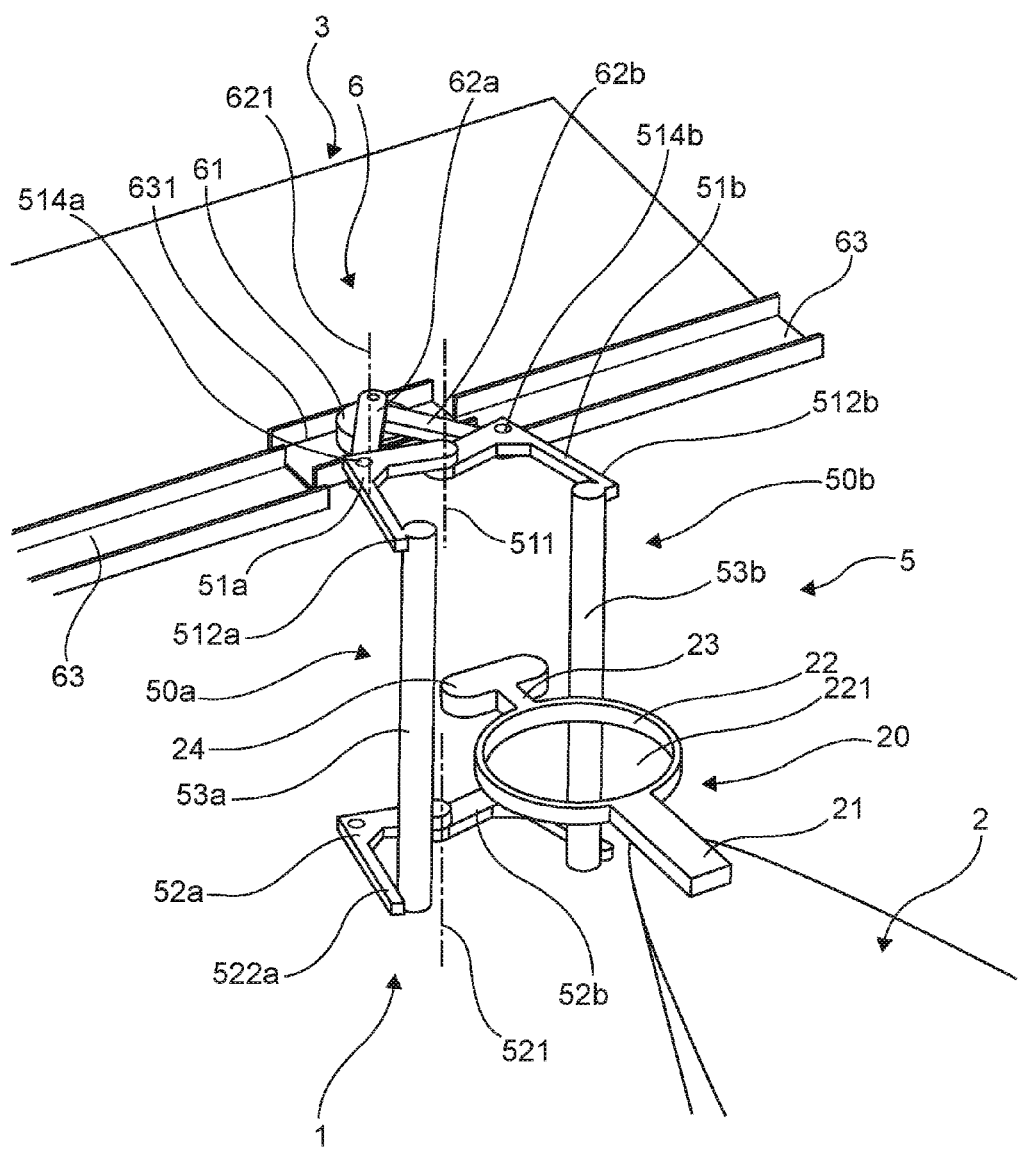
FIG. 2 is a three-quarter view of a mooring device according to a first embodiment on the disclosure in its inactive position.
Figure 3:
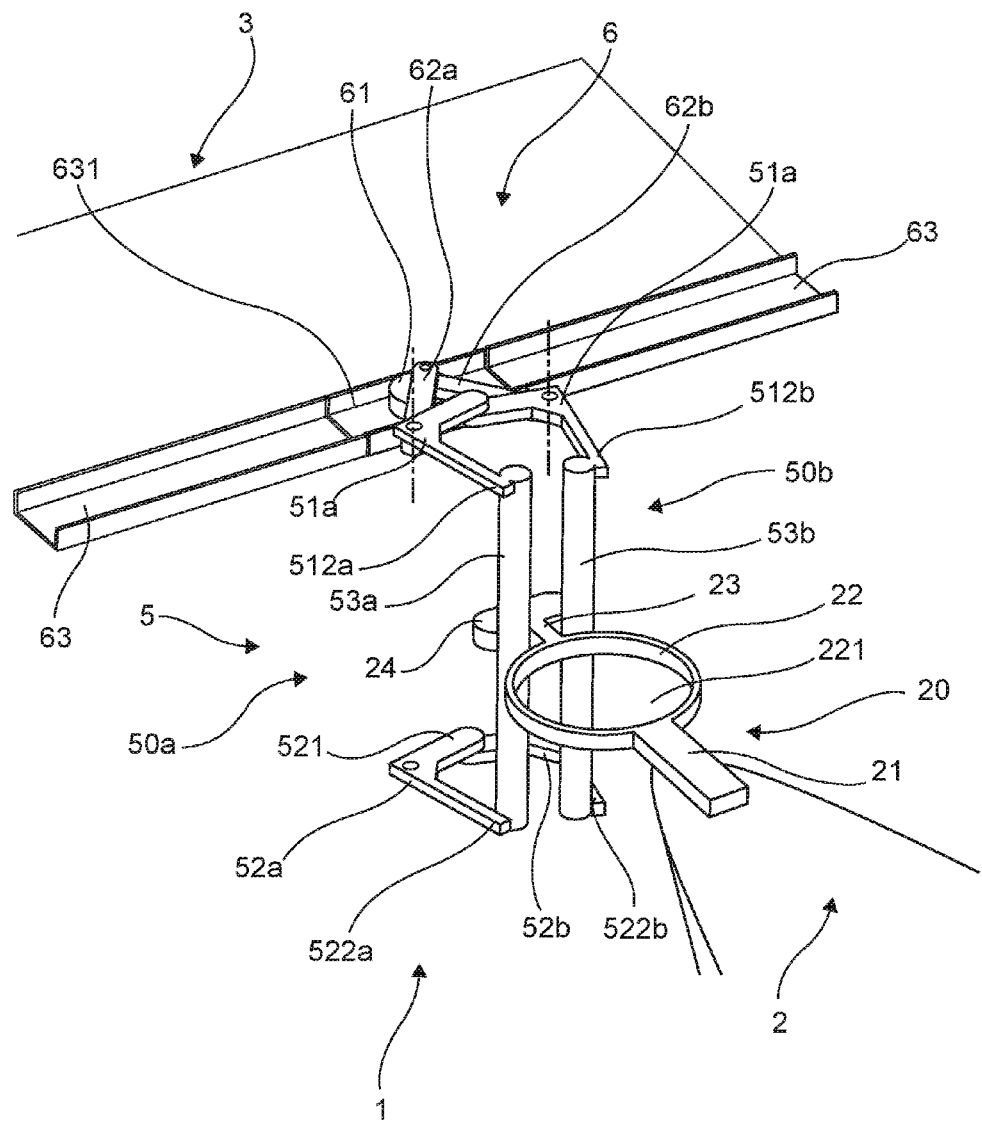
FIG. 3 is a three-quarter view of the mooring device of FIG. 2 in the active position.

A mooring device 1 for mooring a water craft 2 according to a first embodiment is partially represented in the three-quarter views of FIGS. 2 and 3. This mooring device 1 is implemented in a leisure port for example.

It comprises a lock 5 comprising catch jaws 50a and 50b fixedly attached to a floating pontoon 3 and engaging element 20 fixedly attached to a water craft 2 which is moored to the pontoon 3 in FIG. 3.

In this first embodiment, the lock 5 is fixedly attached to the pontoon 3 by means of a profile 63 extending longitudinally along the pontoon 3. The profile 63 can receive a plurality of locks so as to receive a plurality of water craft.

The profile 63 which is fixedly attached to the upper surface of the pontoon 3 herein has a substantially U-shaped section. Naturally, a section of a different shape can be implemented.

The mooring device 1 furthermore comprises an actuator element 6 for actuating the lock 5, comprising an actuator (not shown) which can be commanded manually or automatically. The actuator acts on a mobile portion 631 of the profile 63 thus enabling the shifting of the mobile portion 631 of the profile 63 perpendicularly to the longitudinal axis of this profile 63 in a same plane.

The mobile portion 631 carries a fixed support element 61 on which there are mounted, hinged about a same rotational shaft 621, two levers or tie-rods 62a and 62b which extend towards the water craft 2 to be moored, in forming a variable V corner.

The tie-rods 62a and 62b are respectively fixedly attached to one extremity of an upper bracket 51a and 51b. These brackets 51a, 51b is mounted so as to be mobile in rotation on the levers 62a and 62b respectively about a shaft 513a, 513b situated in the vicinity of the corner/right angle.

Besides, the upper brackets 51a and 51b are connected to each other by means of a pivot link, or rotation shaft 511, situated on a first of their extremities.

The lock 5 comprises, in addition, a pair of lower brackets 52a and 52b which are connected by means of a pivot link or rotation shaft 521 situated at one end of their extremities.

The two pairs of brackets 51a, 51b, 52a, 52b are connected to each other by a pair of catch bars 53a, 53b extending in a plane perpendicular to the plane of the brackets, the levers 62a and 62b, and the profile 63 (and the pontoon 3).

More specifically, the first catch bar 53a is fixed between the respective extremities 512a, 522a of the brackets 51a, 52a. In the same way, the second catch bar 53b is fixed between the respective extremities 512b and 522b (not shown) of the brackets 51b and 52b.

In this embodiment, the lower brackets 52a, 52b are not fixedly attached to the pontoon 3. In one variant, these brackets 52a, 52b are fixedly attached to the pontoon in a manner similar to the upper brackets 51a and 51b.

The assembly constituted by the bars 53a, 53b and the brackets 51a, 51b, 52a, 52b thus form two jaws 50a and 50b mobile between an open position (FIG. 2) and a closed position (FIG. 3).

These jaws 50a, 50b can move between an open position (as illustrated in FIG. 2) in which the catch bars 53a, 53b are moved away from each other permitting the insertion or withdrawal of the engaging element 20 (each pair of brackets substantially forming a "W") and a closed position (as illustrated in FIG. 3) in which the catch bars 53a, 53b are brought closer to each other and maintain the engaging element 30 borne by the water craft 2 (each pair of brackets forming appreciably a "U").

The lock 5 comprising jaws 50a, 50b is therefore designed to cooperate with the engaging element 20 fixedly attached to the bow of the water craft 2.

The engaging element 20 comprises a shaft 21 which is fixed to the water craft (by screwing for example) and is extended by a ring-shaped element 22 having an inner opening 221. A pleasure-boat owner or boater situated on the pontoon can thus introduce a boat hook or a pole into the ring 22 so as to pull and guide the water craft 2 towards the lock 5 or to push the water craft 2 away from the pontoon 3.

In one variant, it is planned to implement an automatic pole (not shown) to guide a water craft. This pole is automatically actuated at the approach of the water craft, for example. This pole can be also configured to carry out the reverse movement, i.e. to push the water craft away from the pontoon 3.

The ring 22 is prolonged by a rod or center portion 23 with a reduced section, and is itself extended by a pad or first end portion 24 (in the shape of an oblong slab). The ring 22 forms a second end portion of the engaging element 20.

The rod 23 and the pin 24 are situated so as to be diametrically opposite the shaft 21. The pin 24 extends perpendicularly to the rod 23, these two elements forming a T which is configured to cooperate with the jaws 50a, 50b when these jaws are closed (FIG. 3).

More specifically, as illustrated in FIG. 3, the jaws 50a, 50b get housed between the pin 24 and the ring 22 on each side of the rod 23. Preferably, there is a clearance between the jaws 50a and 50b and the rod 23 so as to allow lateral and vertical play of the rod 23 (in a plane parallel to the pontoon 3 and in a plane perpendicular to this pontoon).

A more detailed description is now provided of the working of the lock 5 and the engaging element 20 with reference to FIGS. 2 and 3. The description here is situated in the context of a maneuver for mooring the water craft 2 to the pontoon 3 which is equipped with the mooring device 1.

When no water craft is moored to the mooring device 1, the lock 5 is placed in an open (or unlocking) position as illustrated in FIG. 2. In this position, the mobile portion 631 of the profile 63 is shifted towards the pontoon 3 relative to the longitudinal axis of the profile 63. The jaws 50a, 50b are open, i.e. they are moved away from each other. In this position, the distance between the jaws 50a, 50b is greater than the width of the pin 24.

It will be understood here that the width of the pin 24 is the distance measured between the two extremities of the pin 24 along an axis perpendicular to the rod 23 and the shaft 21.

When the water craft 2 is approaching the lock 5, a pleasure-boat owner or boater placed on the pontoon can introduce a boat hook into the ring 22 and thus direct the engaging element 20 between the open jaws 50a and 50b.

The ring 22 can also cooperate with a pole actuated automatically, as stressed here above.

Once the pin 24 and the rod 23 are engaged between the open jaws 50a, 50b (FIG. 2), the actuator (activated by hand or automatically) drives the movement of the mobile portion 631 of the profile 63 until the mobile portion 631 is aligned with the longitudinal axis of the profile 63. This shift of the mobile portion 631 prompts the levers 62a, 62b to come closer to each other and therefore prompts a pivoting of the brackets 51a, 51b, 52a, 52b about the axes of rotation 511, 521, thus causing the closing of the jaws 50a, 50b and their positioning between the pin 24 and the ring 22 on each side of the rod 23 (FIG. 3).

The jaws 50a, 50b are then in a locking position and the water craft 2 is fixedly attached to the pontoon 3.

In the closed or locking position of the jaws 50a, 50b the distance between the jaws 50a and 50b is smaller than the width of the pin 24 and the width (or diameter) of the ring 22.

In this same position, the distance between the jaws 50a, 50b is greater than the width of the rod 23 in such a way as to enable the movement of the engaging element 20 along the jaws 50a, 50b and enable the water craft 2 to follow the movements of the water (the oscillations of the waves, especially,) without damaging the link between the water craft 2 and the pontoon 3.

6.2 Description of a Second Embodiment

Figure 4:
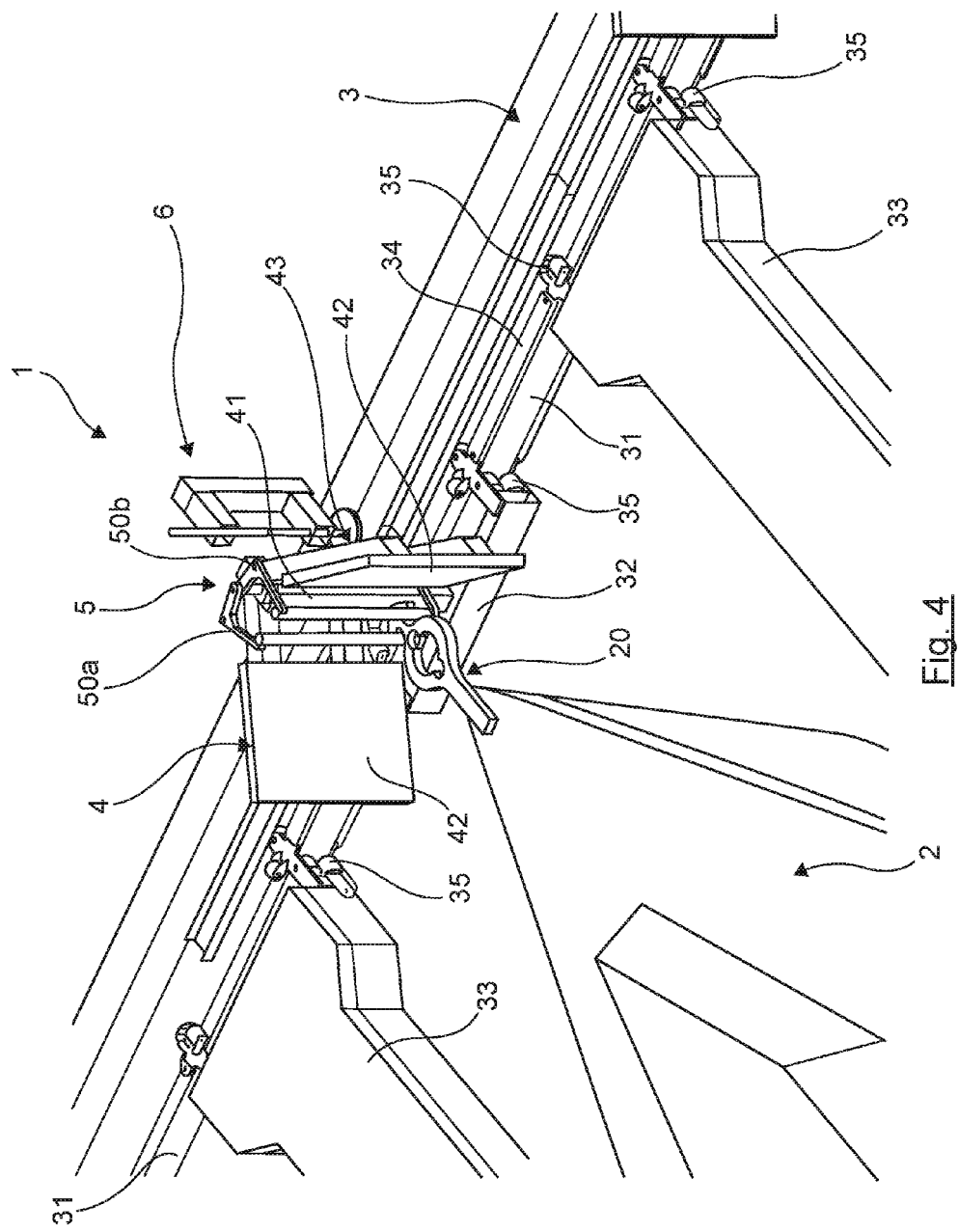
FIG. 4 is an overall three-quarter view of a mooring device according to a second embodiment of the disclosure.
Figure 5:
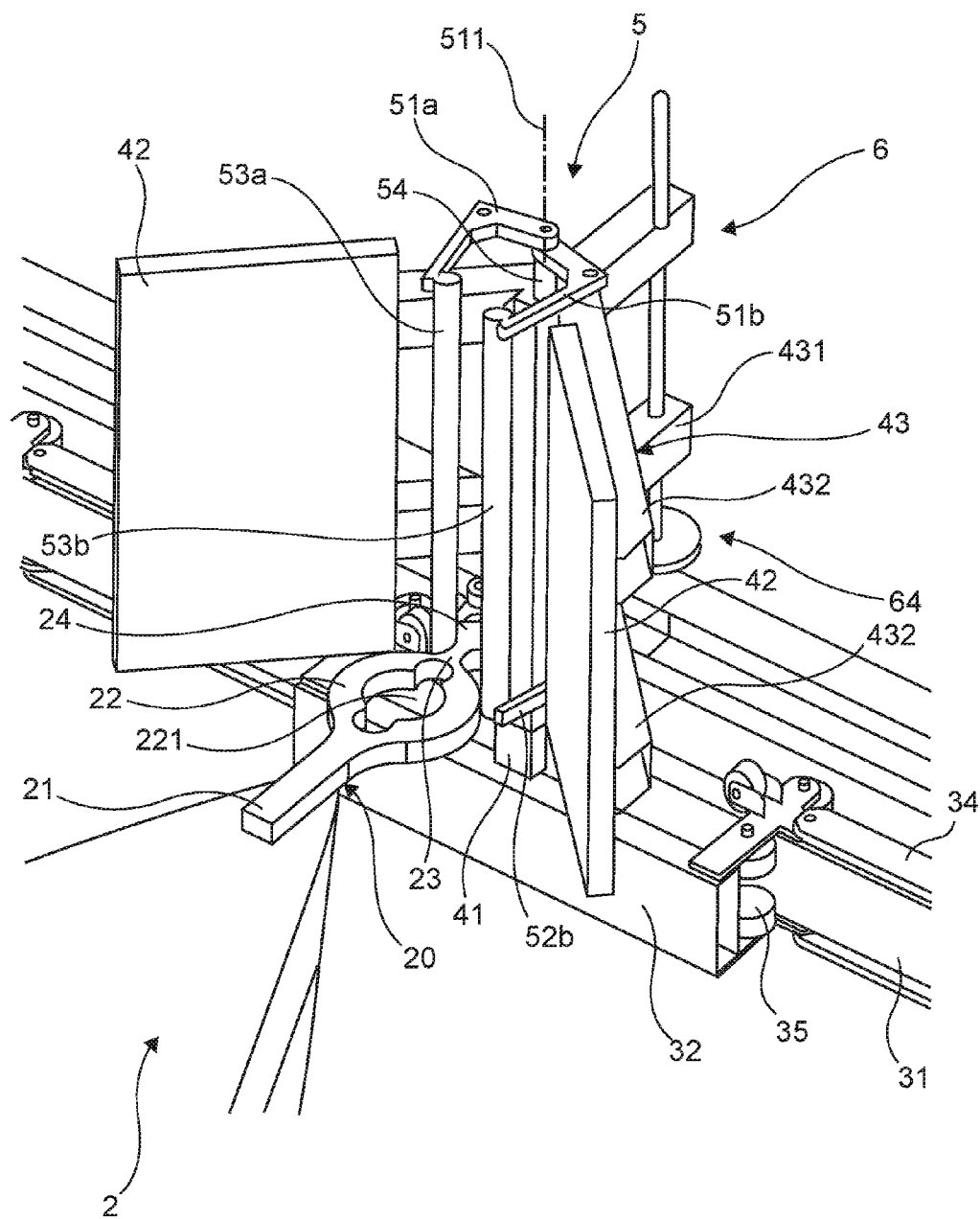
FIG. 5 is a detailed three-quarter view of the mooring device of FIG. 4, in its active position.
Figure 6:
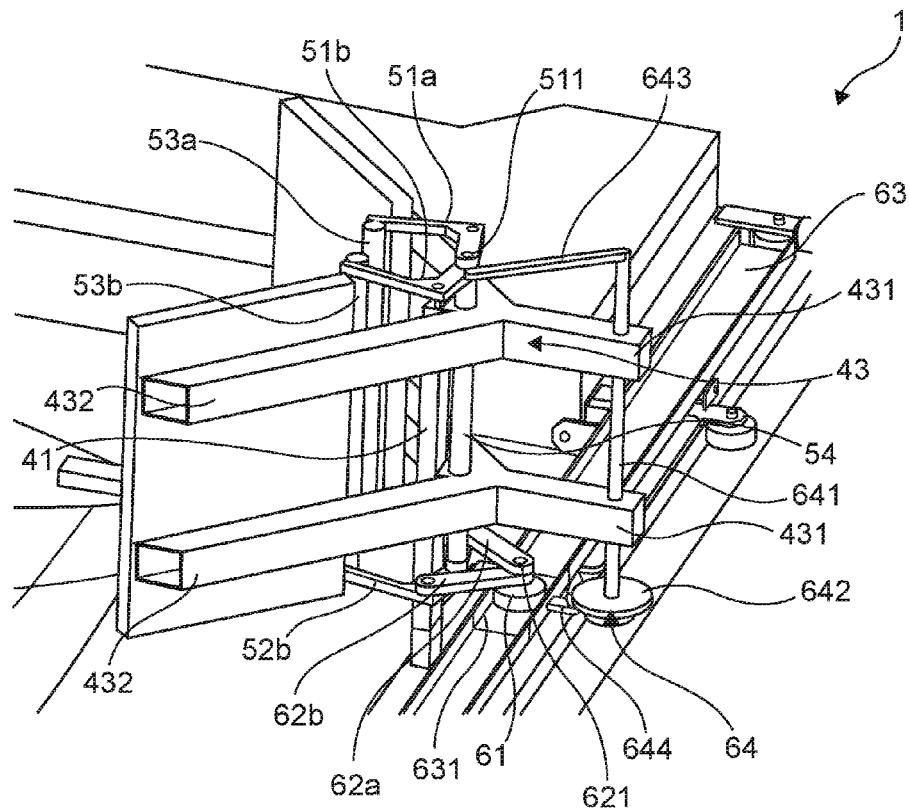
FIG. 6 is a three-quarter view of the mooring device of FIGS. 4 and 5.

A mooring device 1 for mooring a water craft 2 according to a second embodiment is shown in FIGS. 4 to 6.

This mooring device 1 comprises a lock 5 comprising two jaws 50a and 50b (FIG. 4) fixedly attached to a floating pontoon 3 and engaging element 20 fixedly attached to the water craft 2 to be moored to the pontoon 3.

In this second embodiment, the pontoon 3 comprises a shifting element for shifting the lock 5 on the pontoon 3. The shifting element comprises a rail 31 which extends on at least a part of the length of the pontoon 3. The rail 31 has a substantially parallelepiped shape and is an integral part of the pontoon 3 (it can be fixed permanently to the pontoon in one alternative embodiment).

A sliding carriage 32 is mounted so as to be mobile in translation on the rail 31 and is designed especially to support the lock 5 of the mooring device.

The carriage 32 is connected upstream and downstream to a catway 33 extending perpendicularly to the pontoon 3 by means of a cross-member 34 in such a way that the entire mooring device 1 can be shifted along the pontoon 3 on the rail 31.

The shifting of the assembly formed by the carriage 32 and the catway 33 can be done manually or by means of a motor (not shown) and is facilitated by the implementing of a plurality of wheels 35.

A locking system (not shown) for locking the position of the mooring device 1 to the rail 31 is implemented in order to secure the device and prevent lateral shifts of the mooring device 1 due to swells especially.

Besides, the mooring device 1 comprises a chassis 4 bearing a lock 5, the chassis 4 being fixedly attached to the carriage 32.

The chassis 4 comprises a central upright 41 extending perpendicularly to the carriage 32 and carries a guide for centering/guiding which takes the form of two lateral walls or shutters 42. These shutters 42 are rectangular and extend towards the water craft to be moored in forming a V element.

The shutters 42 of the chassis 4 are mounted so as to be fixed to the upright 41 by means of at least one supporting element 43. Here, each of the shutters 42 is fixedly attached to the upright 41 by means of two support elements 43 comprising a base 431 and two arms 432 (forming a Y). More specifically, the shutters 42 are fixedly attached to the arms 432 of the supporting element 43.

The shutters 42 are for directing and/or centering the engaging element 20 borne by the water craft 2 towards or on the lock 5 positioned on the pontoon 3.

The chassis 4, behind the upright 41 and more specifically at the meeting point of the two branches 432 of the supporting element 43, has a circular aperture in which there is mounted a tube 54 carrying jaws 50a, 50b as illustrated in FIG. 6.

In this second embodiment, the structure of the jaws 50a, 50b is identical to the one described in the first embodiment.

The lock 5 thus implements two jaws 50a, 50b which are fixedly attached to the frame 4 by means of two pairs of brackets 51a, 51b and 52a, 52b.

The upper brackets 51a, 51b are mobile in rotation relative to each other by means of a pivot link or rotation shaft 511 situated on a first extremity of each of the upper brackets 51a, 51b.

The lower brackets 52a, 52b are in the same way mobile in rotation relative to each other by means of a pivot link or rotation shaft 521 (which cannot be seen) situated on a first extremity of each of the lower brackets 52a, 52b.

The second extremity of the lower brackets 52a, 52b and the upper brackets 51a, 51b are connected to each other by means of a catch bar 53a, 53b.

The brackets and the catch bars thus form the jaws 50a and 50b.

The carrier tube 54 cooperating with the chassis 4 links the rotation shaft 511 of the upper brackets 51a and 51b to the rotation shaft 521 of the lower brackets 52a and 52b.

Such a carrier tube 54 furthermore makes it possible to rigidify/reinforce the structure of the lock 5.

The mooring device 1 comprises an actuator element 6 for actuating lock 5 comprising a support element (or slab) 61 on which are mounted, hinged on a same rotation shaft 621, two levers or tie-rods 62a and 62b which extend in forming an angle V of variable value, towards the water craft 2 to be moored.

The tie-rods 62a, 62b are respectively fixedly attached at their other extremity to a lower bracket 52a, 52b. These brackets 52a, 52b are mounted so as to be rotationally mobile on the tie-rods 62a, 62b respectively about a rotation shaft that is situated in the vicinity of their corner/right angle.

The support element 61 is fixedly attached to a mobile portion 631 of a profile 63 extending in parallel to the edge of the pontoon 3. The mobile portion 631 is capable of shifting, i.e. shifting in translation perpendicularly to the longitudinal axis of the profile 63 depending on whether it is sought to open or close the jaws 50a, 50b.

In this example the profile 63 is fixedly attached to the carriage 32 and the cross members 34 so as to enable the shifting of the mooring device 1 on the rail 31.

The shifting in translation of the mobile portion 631 of the profile 63 is implemented by an actuator 64.

FIG. 6 illustrates the implementing of a manual activator 64, this actuator 64 being mounted pivotingly on each of the bases 431 of the support element 43 of the chassis 4.

The bases 431 each have a circular aperture enabling the passage of a shaft 641 extending in parallel to the tube 54. The shaft 641 is fixedly attached at its lower extremity to a cam 642 and its upper extremity to a handle 643.

When a user acts on the handle 643 of the actuator 64, the shaft 641 pivots and drives the cam 642 in rotation. The rotation of the cam 642 prompts the shifting of the mobile portion 631 by means of a rod 644 connecting the cam 642 and the mobile portion 631. More specifically, the mobile portion 631 which is herein disposed along the longitudinal axis of the profile 63 gets offset and shifted towards the cam 642.

As a result of this, the angle between the rods 62a and 62b diminishes prompting the opening/moving apart of the jaws 50a, 50b. It will be understood that the shifting of the handle 643 in the other sense closes/brings nearer the jaws 50a, 50b.

The actuator 64 thus enables the shifting of the jaws 50a, 50b between the open position in which the catch bars are moved away from each other permitting the passage of the engaging element 20 (the upper and lower brackets respectively form a "W") and a closed position (as illustrated in FIGS. 5 and 6) in which the catch bars 53a, 53b are brought close to each other and maintain the engaging element 20 (the upper and lower brackets respectively forming a "U").

The assembly comprising the actuator 64, the drive cam 642, the pair of tie-rods 62a, 62b, the support element 61 and the mobile portion 631 form actuator element 6 for actuating lock 5 for locking the mooring device 1.

Just as in the first embodiment, the lock 5 cooperates with engaging element 20.

As illustrated in FIG. 5, the engaging element 20 comprises a shaft 21 connecting the water craft 2 to be moored with a ring 22 which has an inner opening 221. The purpose of the opening 221 is to cooperate with a manual or automatic pole used to bring the water craft 2 closer to the lock 5 or to move it away.

The opening 221 is formed by a circular aperture extended by two grooves on the opposite edges situated in the extension of the shaft 21. Naturally, this opening 221 can be circular or take another form. The engaging element 20 also comprises a rod, or central portion 23 of smaller width. A first end of the rod 23 is fixedly attached to the ring 22 and a second end of the rod 23 is connected to a pin 24.

The mooring of the water craft 2 to the pontoon 3 is obtained when the pin 24 is introduced between the jaws 50a, 50b which are open and when the jaws are moved away until the insertion of the central rod 23 (with a clearance) as illustrated in FIG. 5.

6.3 Description of the Third Embodiment

Figure 8A:
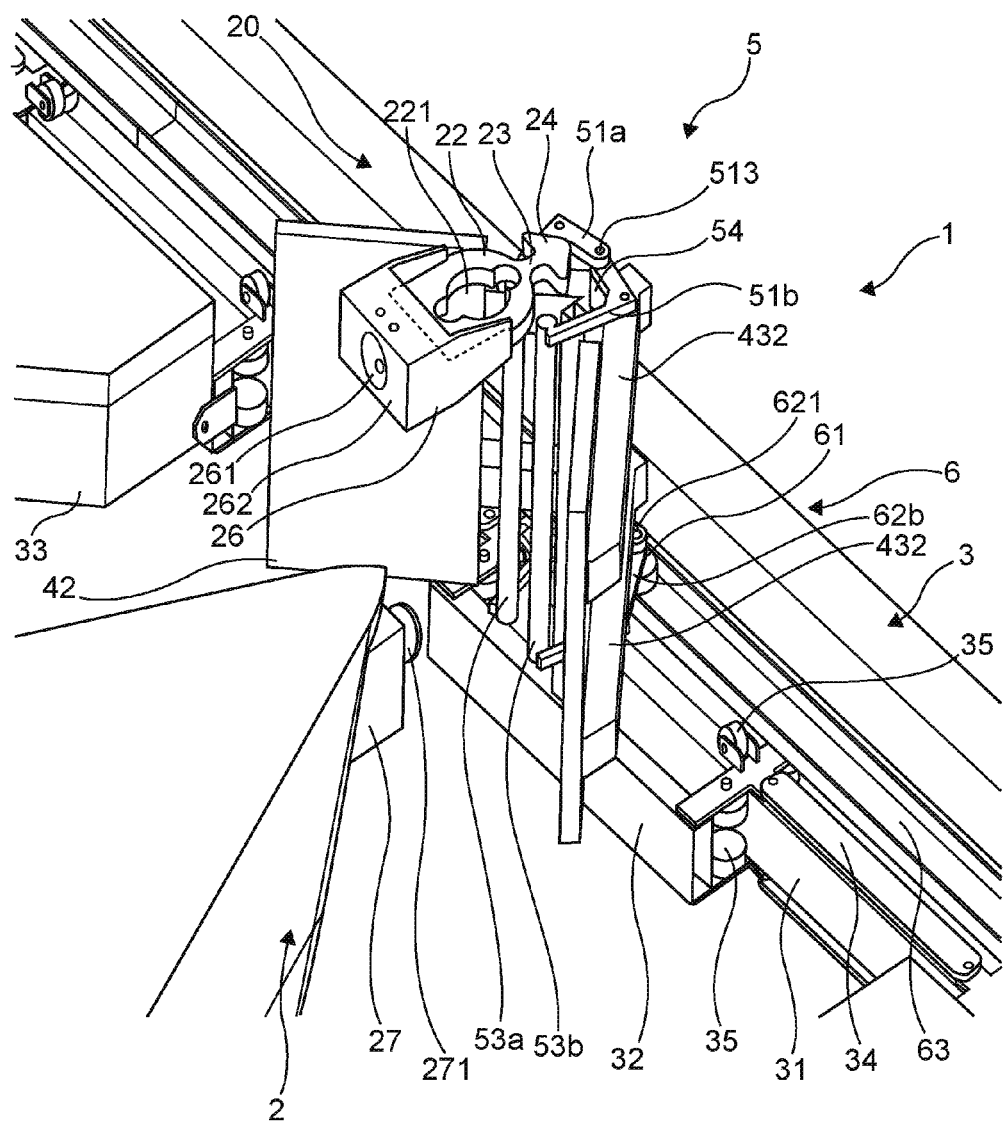
FIGS. 8A and 8B are three-quarter views of a mooring device according to a third embodiment of the disclosure.
Figure 8B:
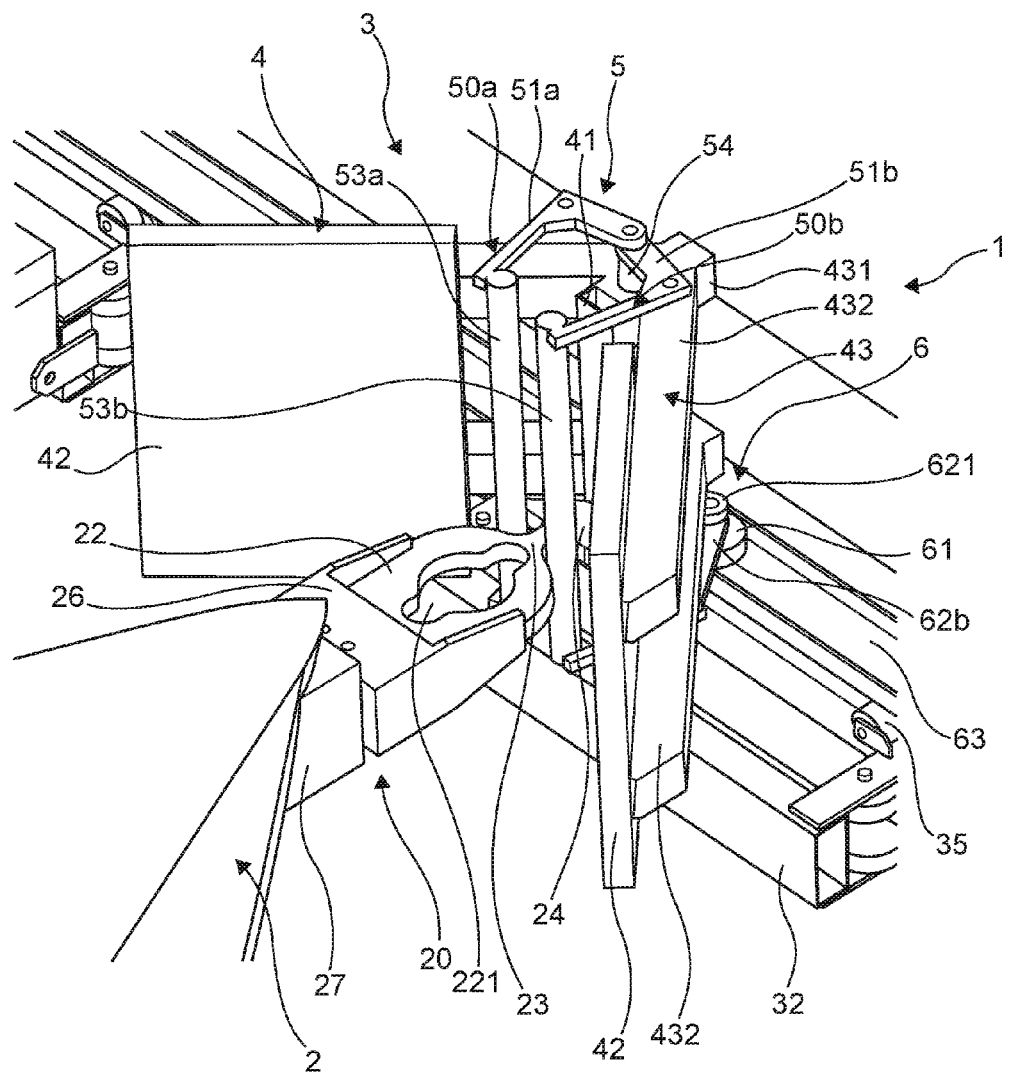

A mooring device 1 for mooring a water craft according to the third embodiment is shown in FIGS. 8A and 8B.

This mooring device 1 has a lock 5 formed by two jaws 50a, 50b fixedly attached to a floating pontoon 3 and engaging element 20 fixedly attached to the water craft 2 to be moored to the pontoon 3.

This third embodiment differs from the first two embodiments described above in that the jaws 50a and 50b of the lock 5 remains in a closed position during the mooring and unmooring of the water craft 2.

In this third embodiment and similarly to the second embodiment, the pontoon 3 has a shifting element for shifting the lock 5 along the pontoon 3. The shifting element comprises a rail 31 which extends on at least one part of the length of the pontoon 3. A sliding carriage 32 is mounted so as to be mobile in translation on the rail 31 and is especially meant for supporting the lock 5 of the mooring device 1.

The carriage 32 is connected upstream and downstream to a catway 33 extending perpendicularly to the bridge 3 by means of a cross-member 34 in such a way that the mooring device 1 can be shifted along the pontoon 3 on the rail 31.

The shifting of the assembly formed by the carriage 32 and the catway 33 is facilitated by the implementation of a plurality of wheels 35.

A locking system (not shown) for locking the position of the mooring device 1 to the rail 31 is implemented in order to secure the device and prevent lateral shifts due to swells especially.

Besides, the mooring device 1 comprises a chassis 4 fixedly attached to the carriage 32 and meant for carrying the lock 5.

The chassis 4 has a central upright 41 (visible in FIG. 8B) extending perpendicularly to the carriage 32 and has two side walls or shutters 42 that are substantially rectangular, extending towards the water craft to be moored and forming a V.

The shutters 42 of the frame 4 are mounted so as to be fixed to the upright 41 by means of at least one support element 43. Here, each of the shutters 42 is fixedly attached to the upright 41 by means of the two support elements 43 which are substantially Y-shaped (and comprise a base 431 and two arms 432). More specifically, the shutters 42 are fixedly attached to the arms 432 of the support element 433.

The purpose of the shutters 42 is to direct and/or center the engaging element 20 borne by the water craft 2 towards or on the lock 5 disposed on the pontoon 3.

Behind the upright 41 and more specifically at the meeting point of the two arms 432 of the support element 43, the chassis 4 has a circular aperture in which there is mounted a tube 54 bearing the jaws 50a, 50b.

In this third embodiment, the structure of the jaws 50a, 50b is identical to that described in the first two embodiments.

The lock 5 therefore implements two jaws 50a and 50b fixedly attached to the chassis 4 by means of two pairs of brackets 51a, 51b and 52a, 52b (not shown).

The brackets and the catch bars 53a, 53b thus form the jaws 50a and 50b.

As illustrated in FIGS. 8A and 8B, the jaws 50a, 50b are in a closed position, the catch bars 53a and 53b being brought closer together and gripping the engaging element 20.

In this third embodiment, the engaging element 20 is in two parts that can be dismantled. More specifically, the engaging element 20 comprises a pedestal, or first fixed part 27, fixedly attached to the water craft 2 and a detachable part or second part 26 for cooperating with the jaws 50a, 50b of the lock 5.

The pedestal 27 which is fixed to the water craft 2 has an engaging pin 273 extending in the extension of the bow of the water craft 2. The purpose of the engaging pin 271 is to cooperate with the circularizing 261 made in the base 262 of the detachable part 26 so as to fixedly attach the base 27 to the detachable part 26.

The detachable part 26 furthermore has a ring 22 comprising an inner opening 221. The opening 221 is designed to cooperate with a manual or automatic pole used to bring the water craft 2 closer to the lock 5 or to move it away from the lock 5.

The opening 221 is formed by a circular aperture extended by two grooves on the opposite edges situated in the extension of the circular housing 261.

Naturally, this opening 221 can be circular or can take any other shape.

The detachable part 26 also has a rod or central portion 23 of reduced width. A first extremity of the rod 23 is fixedly attached to the ring 22 and a second extremity of the rod 23 is fixedly attached to an arrow-shaped feature 24.

The mooring of the water craft 2 to the pontoon 3 calls for the following operations:
- the pleasure-boat owner or boater must first dismantle/detach the detachable part 26 from its pedestal 27 (as illustrated in FIG. 8A);
- the pleasure-boat owner or boater must then insert, from the top and by the bottom, the arrow-shaped feature 24 of the engaging element 20 towards the closed jaws 50a, 50b of the lock 5. Once this operation has been done, the jaws 50a, 50b are situated on either side of the rod 23, and
- the pleasure-boat owner or boater must finally re-mount and fixedly attach the detachable part 26 to the pedestal 27 of the water craft 2 (as shown in FIG. 8B).

Once the pedestal 27 and the detachable part 26 of the engaging element are fixedly attached to each other, the water craft 2 is solidly moored to the pontoon 3.

The unmooring of the water craft 2 requires the following operations:
- the pleasure-boat owner or boater must first dismount/detach the detachable part 26 from its pedestal 27;
- the pleasure-boat owner or boater must then withdraw, by the top or by the bottom, the arrow-shaped feature 24 from the closed jaws 50a, 50b, and
- the pleasure-boat owner or boater must then remount/fixedly attach the detachable part 26 to the pedestal 27 of the water craft 2 (as illustrated in FIG. 8B).

6.4 Description of a Fourth Embodiment

Figure 9A:
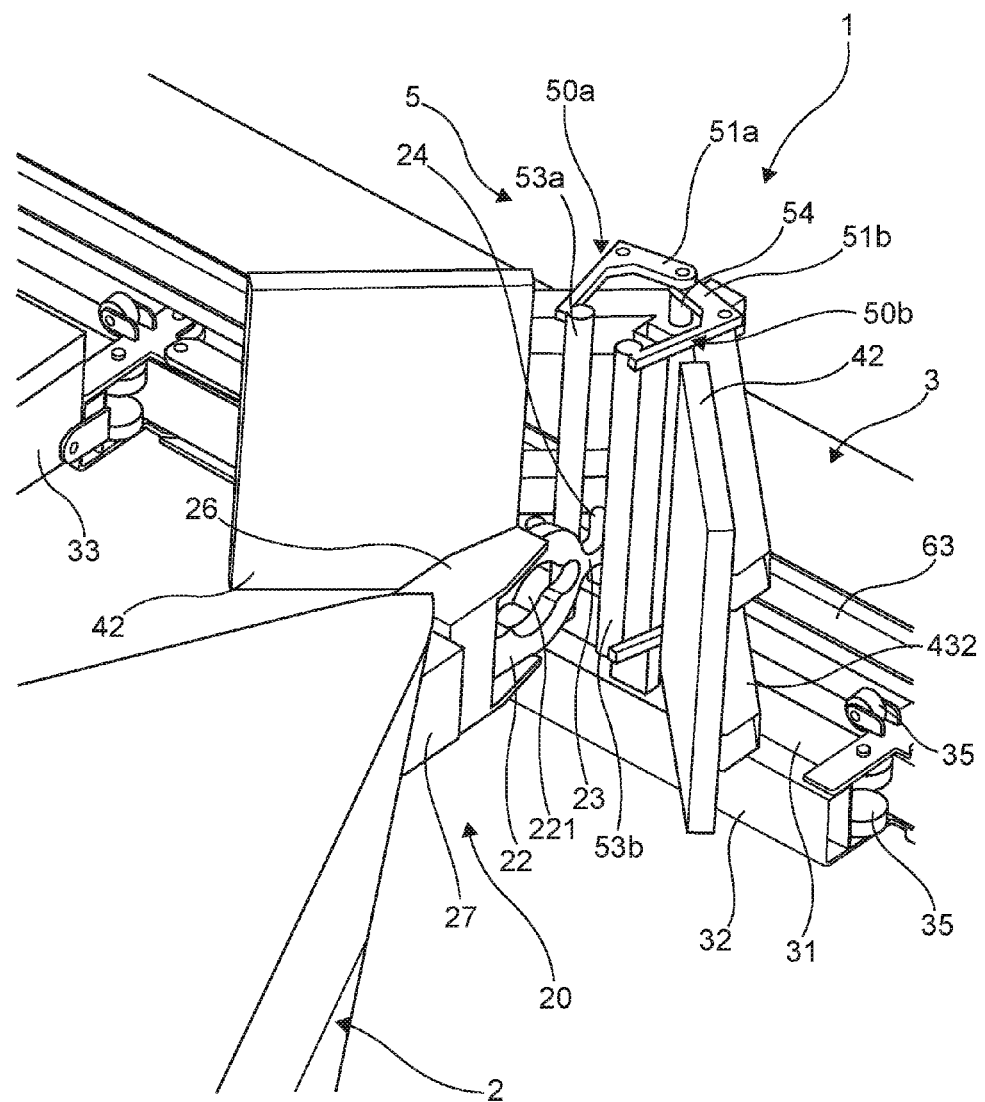
FIGS. 9A and 9B are three-quarter views of a mooring device according to a fourth embodiment of the invention.
Figure 9B:
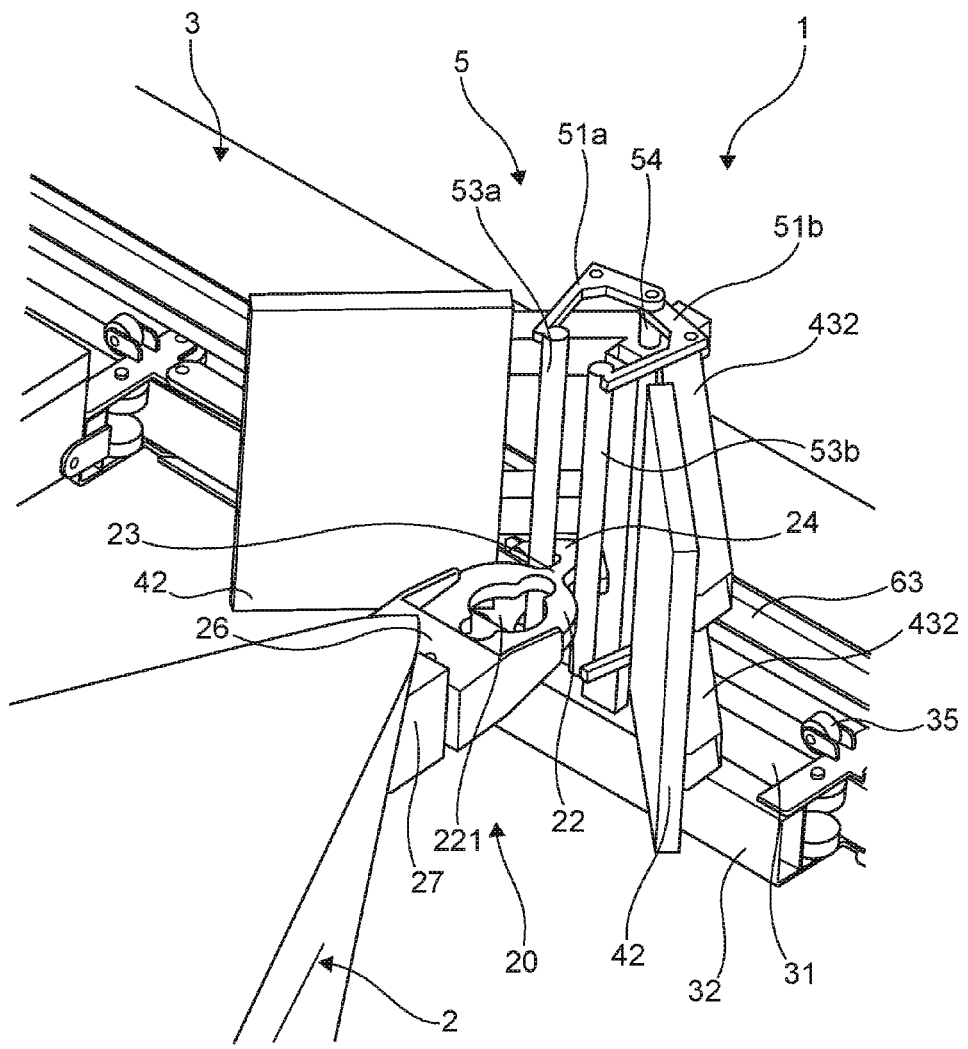

A mooring device 1 for mooring a water craft 2 according to a fourth embodiment is shown in FIGS. 9A and 9B.

This mooring device 1 comprises a lock 5 comprising two jaws 50a, 50b fixedly attached to a floating pontoon 3 and engaging element 20 fixedly attached to the water craft 2 to be moored to the pontoon 3.

In this fourth embodiment, the jaws 50a and 50b of the lock 5 remain in a closed position during the mooring and unmooring of the water craft 2.

This fourth embodiment differs from the third embodiment described above in that the second part 26 of the engaging element 20 of the water craft 2, designed to cooperate with the jaws 50a, 50b of the lock 5, is mounted so as to be rotationally mobile on the pedestal, or fixed part 27, which is fixedly and permanently attached to the bow of the water craft 2. This second part 26 is mounted so as to be either detachable or not detachable on the fixed part 27.

Identically to the above embodiment, the pivoting part 26 comprises a ring 22 having an inner opening 221. The opening 221 is meant for cooperating with a manual or automatic pole enabling the water craft 2 to be brought closer to or moved away from the lock 5.

The opening 221 is formed by a circular aperture extended by two grooves on the opposite edges situated in the extension of the pedestal 27. Naturally, this opening 221 can be circular and have another shape.

The pivoting part 26 also has a rod or central portion 23 of a reduced width. A first extremity of the rod 23 is fixedly attached to the ring 22 and a second extremity of the rod 23 is connected to an arrow-shaped feature 24.

The mooring of the water craft 2 to the pontoon 3 is simple and requires few operations.

Indeed, in an inactive position, the pivoting part 23 is oriented vertically relative to the upper surface of the bridge of the water craft 2 (as illustrated in FIG. 9A). This first orientation of the pivoting part 26 enables the arrow-shaped feature 24 to slide between the jaws 50a, 50b of the lock 5 situated on the pontoon 3.

When the arrow-shaped feature 24 goes beyond the jaws 50a and 50b, the pivoting part 26 pivots by 90° to pass into the active position so as to block/lock the arrow-shaped feature 24 of the water craft 2 (as illustrated in FIG. 9B). In this position, the rod 23 of the engaging element is situated between the catch bars 53a, 53b of the lock 5.

The pivoting of the pivoting part 26 is obtained by a manual action on the part of the user.

In one variant, the pivoting can be automatic or triggered by a remote control unit situated in the control room or bridge of the water craft for example.

6.5 Other Aspects and Alternatives

Figure 7:
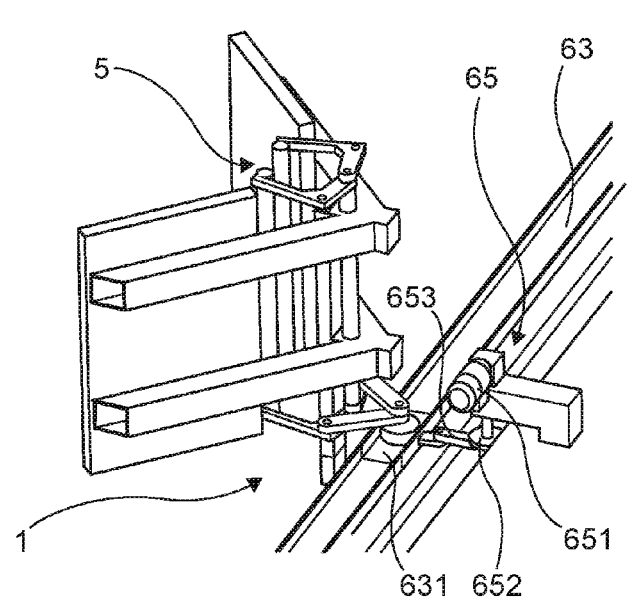
FIG. 7 illustrates a variant of the actuator for actuating the mooring device according to the disclosure.

In one variant of the disclosure, illustrated in FIG. 7, the actuator element 6 for actuating the lock 5 implements an automatic actuator 65 comprising a motor 651. The purpose of the motor 651 is to shift the cam 652 in rotation, this cam acting on a rod 653 fixedly attached to the mobile part 631 so as to enable the shifting of the mobile part 631 relative to the longitudinal axis of the profile 63.

The closing of the jaws can be initiated by the actuator when detection means (comprising one or more sensors) determine that the engaging element is accurately positioned between the jaws.

The actuator can be commanded by a remote control situated for example in the control room of the water craft.

It can be noted that the engaging element can be situated in the rear or on the sides of the water craft.

For example, the ring 22 of the engaging element can be replaced by a triangular element enabling optimized guiding of the jaws on each side of the rod during the closing of the jaws. In one variant, it is possible for the engaging element 20 not to include any ring, the pin 34 being directly connected to the bow of the water craft 2.

In one variant of the embodiments described above, the lock can be borne by the water craft and the engaging element can be fixedly attached to the pontoon.

The mooring device according to the disclosure can especially be implemented at sea, on a lake or in a river on a pontoon or on a wharf of a leisure harbor (or a harbor made along a canal or a navigable river), for example. It is particularly but not exclusively suited to pleasure boats.

It must be noted that one and the same pontoon can be equipped with several mooring devices and comprise for example one or more mooring devices with manual actuator and/or one or more mooring devices with automatic actuator.

An exemplary embodiment of the present disclosure overcomes at least certain drawbacks of the prior art.

More specifically, at least one embodiment facilitates the mooring of a boat to a mooring berth of a wharf or a pontoon, especially for a user (a pleasure-boat owner or boater especially) who would be alone on board.

At least one embodiment provides a mooring device that is of simple design (and therefore low in cost), reliable, robust, secure and eliminates or at least minimizes risks for the user.

At least one embodiment provides a mooring device of this kind that can adapt to movements of the water and to variable sizes of water craft.

Although the present disclosure has been described with reference to one or more examples, workers skilled in the art will recognize that changes may be made in form and detail without departing from the scope of the disclosure and/or the appended claims.

The invention claimed is:

1. A mooring device for mooring a water craft to a mooring berth, comprising:
    an engaging element borne by said water craft or said mooring berth; and
    a lock borne by said mooring berth or said water craft, respectively,
    said lock comprising first and second catch bars spaced out and extending vertically, at least a part of the engaging element being adapted to engage between the first and second bars so as to be held by said lock and enable the mooring of the water craft to the mooring berth,
    wherein said first and second catch bars are mobile relative to each other between a locking position in which the first and second catch bars are brought closer to each other and maintain said engaging element and an unlocking position in which the first and second catch bars are moved apart to enable the removal or insertion of said engaging element, and
    wherein the engaging element is movable vertically along the first and second catch bars when the lock is in the locking position.

2. The mooring device according to claim 1, wherein said engaging element comprises a first end portion connected by a central portion of small width to a second end portion, this second end portion being connected to the water craft or to the mooring berth.

3. The mooring device according to claim 2, wherein said second end portion has an opening cooperating with a pole for berthing or for moving the water craft to a distance.

4. The mooring device according to claim 2, wherein, in the locking position of the first and second catch bars, these catch bars are situated on either side of said central portion.

5. The mooring device according to claim 2, wherein said first end portion is disposed on a first side of the first and second catch bars, a space between the first and second catch bars in the locking position being smaller than a width of said first end portion.

6. The mooring device according to claim 2, wherein a space between the first and second catch bars in the locking position is greater than a width of said central portion.

7. The mooring device according to claim 2, wherein a space between the first and second catch bars in the locking position is smaller than a width of said second end portion.

8. The mooring device according to claim 1, wherein said engaging element comprises a first fixed part fixedly attached to said water craft or said mooring berth and a second part mounted detachably on the first fixed part and meant for cooperating with the lock.

9. The mooring device according to claim 1, wherein said engaging element comprises a first fixed part fixedly attached to said water craft or to said mooring berth and a second part mounted pivotingly on said first fixed part and meant for cooperating with the lock.

10. The mooring device according to claim 1, wherein each of the first and second catch bars bears, on at least one of its ends, a bracket mounted pivotingly with a corresponding bracket of the other of the first or second catch bar, the first and second catch bars and the brackets thus forming first and second mobile jaws.

11. The mooring device according to claim 10, wherein said lock comprises an actuator acting on at least one bracket of each of the first and second jaws.

12. The mooring device according to claim 11, wherein said actuator comprises a pair of tie-rods mounted pivotingly about a same shaft at a first of their extremities, each of said tie-rods being mounted pivotingly, at a second extremity, on a distinct bracket of one of said first and second jaws.

13. The mooring device according to claim 12, wherein said tie-rods are mounted pivotingly at their first extremity on a support mobile in translation so as to make the opening angle between the two tie-rods vary.

14. The mooring device according to claim 13, wherein the support is connected to an actuating cam by a rod.

15. The mooring device according to claim 14, wherein said cam is moved by a motor.

16. The mooring device according to claim 14, wherein said cam is moved by a handle connected to said cam by a shaft.

17. The mooring device according to claim 1, wherein the device further comprises a guide, which centers and guides the engaging element towards the lock situated on either side of the first and second catch bars.

18. The mooring device according to claim 1, wherein said lock is mobile relative to said mooring berth when borne by the mooring berth.

19. The mooring device according to claim 18, wherein said lock is borne by at least one carriage capable of shifting in translation on a rail, said rail being mounted so as to be fixed to the mooring berth.

20. A pontoon comprising:
    a mooring berth; and
    one or more mooring devices for mooring a water craft to the mooring berth, each mooring device comprising:
        an engaging element borne by said water craft or said mooring berth; and a lock borne by said mooring berth or said water craft, respectively, said lock comprising first and second catch bars spaced out and extending vertically, at least a part of the engaging element being adapted to engage between the first and second bars so as to be held by said lock and enable the mooring of the water craft to the mooring berth, wherein said first and second catch bars are mobile relative to each other between a locking position in which the first and second catch bars are brought closer to each other and maintain said engaging element and an unlocking position in which the first and second catch bars are moved apart to enable the removal or insertion of said engaging element, and wherein the engaging element is movable vertically along the first and second catch bars when the lock is in the locking position.

21. The mooring device according to claim 1, wherein said first and second catch bars are mobile relative to each other about at least one vertical axis of rotation, between the locking position and the unlocking position.

\* \* \* \* \*